United States Patent [19]

Pöllinger et al.

[11] Patent Number: 5,023,257

[45] Date of Patent: Jun. 11, 1991

[54] INTRAMUSCULAR INJECTION FORMS OF GYRASE INHIBITORS

[75] Inventors: Norbert Pöllinger, Odenthal; Peter Serno, Bergisch Gladbach; Wolfram Hofmann, Bonn; Dieter Beermann, Wuppertal, all of Fed. Rep. of Germany

[73] Assignee: Bayer Aktiengesellschaft, Leverkusen, Fed. Rep. of Germany

[21] Appl. No.: 549,664

[22] Filed: Jul. 6, 1990

Related U.S. Application Data

[63] Continuation of Ser. No. 334,252, Apr. 6, 1989, abandoned.

[30] Foreign Application Priority Data

Apr. 15, 1988 [DE] Fed. Rep. of Germany ....... 3812508
Jan. 25, 1989 [DE] Fed. Rep. of Germany ....... 3902079

[51] Int. Cl.$^5$ .................. A61K 9/08; A61K 9/10; A61K 31/47
[52] U.S. Cl. .................. 514/254; 514/362; 514/363; 514/312; 514/937
[58] Field of Search ............... 514/254, 312, 362, 363, 514/937

[56] References Cited

U.S. PATENT DOCUMENTS

| | | | |
|---|---|---|---|
| 4,181,721 | 1/1986 | Speck et al. | 514/943 |
| 4,559,341 | 12/1985 | Peterson et al. | 514/254 |
| 4,559,342 | 12/1985 | Petersen et al. | 514/254 |
| 4,594,357 | 6/1986 | Dell et al. | 514/537 |
| 4,620,007 | 10/1986 | Grohe et al. | 514/254 |
| 4,670,444 | 6/1987 | Grohe et al. | 514/300 |
| 4,705,789 | 11/1987 | Grohe et al. | 514/254 |
| 4,762,831 | 8/1988 | Grohe et al. | 514/230.2 |
| 4,772,605 | 9/1988 | Naik et al. | 514/254 |
| 4,775,668 | 10/1988 | Jefson et al. | 514/183 |
| 4,780,468 | 10/1988 | Bridges et al. | 514/312 |
| 4,792,552 | 12/1988 | Simonovitch | 514/254 |
| 4,803,205 | 2/1989 | Bridges et al. | 514/254 |
| 4,808,583 | 2/1989 | Grohe et al. | 514/254 |
| 4,816,247 | 3/1989 | Desai et al. | 514/943 |
| 4,816,451 | 10/3198 | Schriewer et al. | 514/185 |
| 4,839,355 | 6/1989 | Lesher | 514/230.2 |
| 4,853,225 | 8/1989 | Wahlig et al. | 424/423 |
| 4,855,292 | 8/1989 | Ueda et al. | 514/312 |
| 4,861,779 | 8/1989 | Jefson et al. | 514/249 |
| 4,874,764 | 10/1989 | Ueda et al. | 514/254 |
| 4,880,806 | 11/1989 | Ueda et al. | 514/254 |
| 4,933,335 | 6/1990 | Bridges et al. | 514/254 |

FOREIGN PATENT DOCUMENTS

| | | | |
|---|---|---|---|
| 0564864 | 8/1958 | Belgium. | |
| 0287926 | 4/1288 | European Pat. Off. | 514/312 |
| 0138018 | 4/1985 | European Pat. Off. . | |
| 0210513 | 2/1987 | European Pat. Off. . | |
| 0219784 | 4/2987 | European Pat. Off. . | |

OTHER PUBLICATIONS

Chemical & Pharm. Bulletin, vol. 29, No. 5, May 1981, pp. 1410–1415, "Studies on the Absorption ... Solution in Rats".

*Primary Examiner*—Shep K. Rose
*Attorney, Agent, or Firm*—Sprung Horn Kramer & Woods

[57] ABSTRACT

Ciprofloxacin and related gyrase inhibitors are tolerated well if administered intramuscularly in the form of an aqueous suspension of the betaine form having an approximate neutral pH value or in the form of an oily suspension of the betaine or salts thereof. Oily suspensions which contain the active material in water-soluble form, eventually in form of the hydrochlorides, lactates, mesilates, methanesulfonates and other salts, are capable of releasing the active compound very rapidly, particularly when the wettability of the oily carrier medium is increased by addition of interfacially surface active materials.

15 Claims, 3 Drawing Sheets

INTRAMUSCULAR INJECTION FORMS OF GYRASE INHIBITORS

This application is a continuation, of application Ser. No. 334,252, filed Apr. 6, 1989.

The invention relates to intramuscular injection forms which contain, as the active compound, gyrase inhibitors from the group comprising quinolone- and 1,8-naphthyridone-3-carboxylic acids, their preparation and their use as medicaments.

Tablets for peroral administration and relatively large volume infusion solutions (0.2% strength/50, 100 ml) and infusion concentrates (1% strength/10 ml) containing, for example, ciprofloxacin as the active substance have so far been available. In contrast, no satisfactory formulation has to date been developed for intramuscular administration. Solutions of, for example, ciprofloxacin of up to 5% strength for intramuscular administration are thus very poorly tolerated because of their non-physiological pH in the acid or alkaline range. After intramuscular injection of aqueous acid or alkaline solutions, considerable intolerances and damage up to necroses have been found in the muscular tissue.

Surprisingly, it has now been found that ciprofloxacin is tolerated well following intramuscular administration if it is administered in the form of an aqueous suspension of the betaine form having an approximate neutral pH value or in the form of an oily suspension of the betaine or salts thereof. Moreover it has been found surprisingly that oily suspensions which contain ciprofloxacin in water-soluble form, eventually in form of the hydrochlorides, lactates, mesilates, methanesulfonates and other salts, are capable of releasing the active compound very rapidly, particularly when the wettability of the oily carrier medium is increased by addition of interfacially surface active materials. To the contrary aqueous suspensions which contain the active compound in the form of betaine ensure protracted release of the active compound.

Regulation and control of release of the active compound is possible via choice of particle size and the combination of auxiliaries respectively.

The invention relates to intramuscular injection formulations of gyrase inhibitors containing 0.05 to 70% by weight of a gyrase inhibitor of the general formula

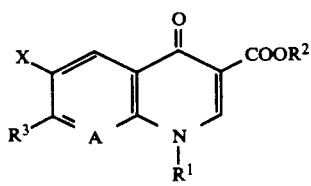

(I)

in which
R$^1$ stands for methyl, ethyl, propyl, isopropyl, cyclopropyl, vinyl, 2-hydroxyethyl, 2-fluoroethyl, methoxy, amino, methylamino, dimethylamino, ethylamino, phenyl, 4-fluorophenyl or 2,4-difluorophenyl,
R$^2$ stands for hydrogen, alkyl having 1 to 4 carbon atoms or (5-methyl-2-oxo-1,3-dioxol-4-yl)-methyl,
R$^3$ stands for methyl or a cyclic amino group, such as

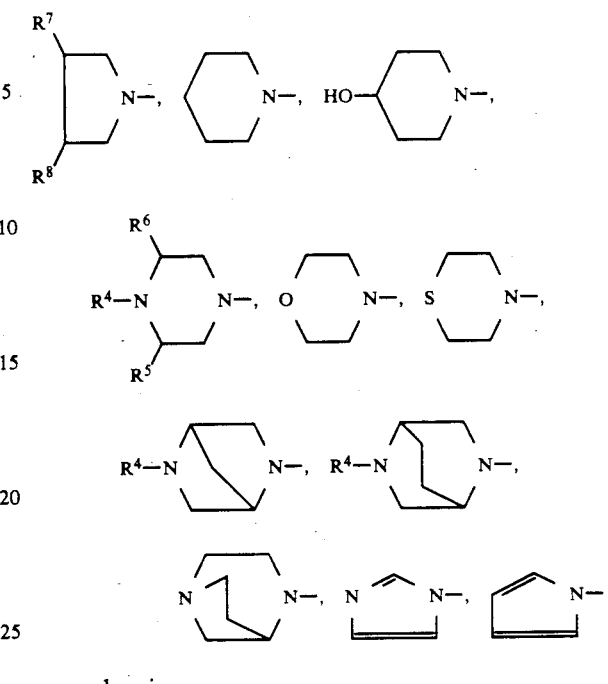

wherein
R$^4$ stands for hydrogen, alkyl having 1 to 4 carbon atoms, 2-hydroxyethyl, allyl, propargyl, 2-oxopropyl, 3-oxobutyl, phenacyl, formyl, CFCl$_2$-S-, CFCl$_2$-SO$_2$-, CH$_3$O-CO-S-, benzyl, 4-aminobenzyl or

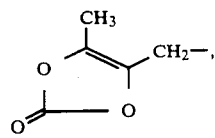

R$^5$ stands for hydrogen or methyl,
R$^6$ stands for hydrogen, alkyl having 1 to 4 carbon atoms, phenyl or benzyloxymethyl,
R$^7$ stands for hydrogen, amino, methylamino, ethylamino, aminomethyl, methylaminomethyl, ethylaminomethyl, dimethylaminomethyl, hydroxyl or hydroxymethyl and
R$^8$ stands for hydrogen, methyl, ethyl or chlorine,
X stands for fluorine, chlorine or nitro and
A stands for N or C-R$^6$,
wherein
R$^6$ stands for hydrogen, halogen, such as fluorine or chlorine, methyl or nitro or, together with
R$^1$, can also form a bridge having the structure

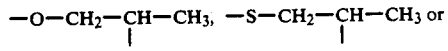

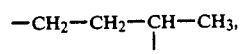

if appropriate as a salt with an acid or base or as a pro-drug, in aqueous or oily suspension.

Not only a systemic action, which can be controlled with respect to time, depending on the composition of the formulation, can be achieved with the intramuscular injections containing gyrase inhibitors. In addition, local infection foci can also be reached by the direct route and treated in a targeted manner over relatively long periods of time.

The gyrase inhibitors can be used in the aqueous and oily injection forms as such or as a salt with an acid or base. It is also possible to use them as a prodrug, for example in the form of esters.

The formulations according to the invention contain 0.05–70% by weight, preferably 2.5–50% by weight, of the active compound.

The suspensions according to the invention for intramuscular injection particularly preferably contain 10–60% weight/weight of the active compound of the above formula.

The formulations mentioned contain, in particular, ciprofloxacin, norfloxacin, pefloxacin, amifloxacin, pirfloxacin, ofloxacin, fleroxacin, lomefloxacin and/or enoxacin. The formulations according to the invention especially preferably also contain the active compounds of European Patent Applications 153,163, 106,489, 153,828, 195,316, 167,763 and 126,355.

The following active compounds may be mentioned in particular: 6-chloro-7-[3-(4-chlorophenyl)-1-piperazinyl]-1-cyclopropyl-8-fluoro-1,4-dihydro-4-oxo-3-quinolinecarboxylic acid, 6-chloro-1-cyclopropyl-8-fluoro-7-[3-(4-fluorophenyl)-1-piperazinyl]-1,4-dihydro-4-oxo-3-quinolinecarboxylic acid, 7-[3-(4-bromophenyl)-1-piperazinyl]-6-chloro-1-cyclopropyl-8-fluoro-1,4-dihydro-4-oxo-3-quinolinecarboxylic acid, 6-chloro-1-cyclopropyl-8-fluoro-1,4-dihydro-7-[3-(4-methylphenyl)-1-piperazinyl]-4-oxo-3-quinolinecarboxylic acid, 7-[3-(4-biphenylyl)-1-piperazinyl]-6-chloro-1-cyclopropyl-8-fluoro-1,4-dihydro-4-oxo-3-quinolinecarboxylic acid, 6-chloro-1-cyclopropyl-8-fluoro-1,4-dihydro-7-[3-(4-methoxyphenyl)-1-piperazinyl]-4-oxo-3-quinolinecarboxylic acid, 6-chloro-1-cyclopropyl-8-fluoro-1,4-dihydro-7-[3-(4-hydroxyphenyl)-1-piperazinyl]-4-oxo-3-quinolinecarboxylic acid, 8-chloro-1-cyclopropyl-6-fluoro-1,4-dihydro-4-oxo-7-(3-phenyl-1-piperazinyl)-3-quinolinecarboxylic acid, 8-chloro-1-cyclopropyl-6-fluoro-1,4-dihydro-4-oxo-7-[(4-nitrophenyl)-1-piperazinyl]-3-quinolinecarboxylic acid, 8-chloro-1-cyclopropyl-6-fluoro-1,4-dihydro-4-oxo-7-[3-(4-piperidinophenyl)-1-piperazinyl]-3-quinolinecarboxylic acid, 8-chloro-1-cyclopropyl-6-fluoro-1,4-dihydro-4-oxo-8-[3-(3,4-dimethoxyphenyl)-1-piperazinyl]-3-quinolinecarboxylic acid, 8-chloro-1-cyclopropyl-6-fluoro-1,4-dihydro-4-oxo-7-[3-(3,4,5-trimethoxyphenyl)-1-piperazinyl]-3-quinolinecarboxylic acid, 8-chloro-1-cyclopropyl-6-fluoro-1,4-dihydro-4-oxo-7-[3-(2-thienyl)-1-piperazinyl]-3-quinolinecarboxylic acid, 8-chloro-1-cyclopropyl,6-fluoro-1,4-dihydro-4-oxo-7-piperidino-3-quinolinecarboxylic acid, 7-(3-amino-1-pyrrolidinyl)-8-chloro-1-cyclopropyl-6-fluoro-1,4-dihydro-4-oxo-3-quinolinecarboxylic acid (active compound B), 6,8-dichloro-1-cyclopropyl-1,4-dihydro-4-oxo-7-(1-piperazinyl)-3-quinolinecarboxylic acid, 7-(4-acetyl-1-piperazinyl)-6,8-dichloro-1-cyclopropyl-1,4-dihydro-4-oxo-3-quinolinecarboxylic acid, 7-(4-acetyl-1-piperazinyl)-6-chloro-1-cyclopropyl-8-fluoro-1,4-dihydro-4-oxo-3-quinolinecarboxylic acid, 6-chloro-1-cyclopropyl-8-fluoro-1,4-dihydro-7-(4-isopropyl-1-piperazinyl)-4-oxo-3-quinolinecarboxylic acid, 6-chloro-1-cyclopropyl-8-fluoro-1,4-dihydro-4-oxo-7-morpholino-3-quinolinecarboxylic acid, 6-chloro-1-cyclopropyl-8-fluoro-1,4-dihydro-4-oxo-7-thiomorpholino-3-quinolinecarboxylic acid, 8-chloro-1-cyclopropyl-7-(4-ethyl-3-oxo-1-piperazinyl)-6-fluoro-1,4-dihydro-4-oxo-3-quinolinecarboxylic acid, 1-cyclopropyl-6,8-difluoro-1,4-dihydro-4-oxo-7-(1-piperazinyl)-3-quinolinecarboxylic acid, 1-cyclopropyl-6,8-difluoro-1,4-dihydro-4-oxo-7-(4-methyl-1-piperazinyl)-3-quinolinecarboxylic acid, 1-cyclopropyl-6,8-difluoro-1,4-dihydro-4-oxo-7-(4-ethyl-1-piperazinyl)-3-quinolinecarboxylic acid, 1-cyclopropyl-6,8-difluoro-1,4-dihydro-4-oxo-7-(3-methyl-1-piperazinyl)-3-quinolinecarboxylic acid, 1-cyclopropyl-6,8-difluoro-1,4-dihydro-4-oxo-7-(3,4-dimethyl-1-piperazinyl)-3-quinolinecarboxylic acid, 1-cyclopropyl-6,8-difluoro-1,4-dihydro-4-oxo-7-(4-ethyl-3-methyl-1-piperazinyl)-3-quinolinecarboxylic acid, 1-cyclopropyl-6,8-difluoro-1,4-dihydro-4-oxo-7-[4-(2-hydroxyethyl)-3-methyl-1-piperazinyl]-3-quinolinecarboxylic acid, 1-cyclopropyl-6,8-difluoro-1,4-dihydro-4-oxo-7-[4-(3-hydroxypropyl)-3-methyl-1-piperazinyl]-3-quinolinecarboxylic acid, 1-cyclopropyl-6,8-difluoro-1,4-dihydro-4-oxo-7-(2,5-dimethyl-1-piperazinyl)-3-quinolinecarboxylic acid, 1-cyclopropyl-6,8-difluoro-1,4-dihydro-4-oxo-7-(4-ethyl-2,5-dimethyl-1-piperazinyl)-3-quinolinecarboxylic acid, 1-cyclopropyl-6,8-difluoro-1,4-dihydro-4-oxo-7-(3,5-dimethyl-1-piperazinyl)-3-quinolinecarboxylic acid (active compound A), 1-cyclopropyl-6,8-difluoro-1,4-dihydro-4-oxo-7-(3,4,5-trimethyl-1-piperazinyl)-3-quinolinecarboxylic acid, 1-cyclopropyl-6,8-difluoro-1,4-dihydro-4-oxo-7-(4-ethyl-3,5-dimethyl-1-piperazinyl)-3-quinolinecarboxylic acid, 1-cyclopropyl-6,8-difluoro-1,4-dihydro-4-oxo-7-(3-ethyl-1-piperazinyl)-3-quinolinecarboxylic acid, 1-cyclopropyl-6,8-difluoro-1,4-dihydro-4-oxo-7-(3-n-propyl-1-piperazinyl)-3-quinolinecarboxylic acid, 1-cyclopropyl-6,8-difluoro-1,4-dihydro-4-oxo-7-(3-aminopyrrolidinyl)-3-quinolinecarboxylic acid (active compound C), 1-cyclopropyl-6,8-difluoro-1,4-dihydro-4-oxo-7-(3-isopropyl-1-piperazinyl)-3-quinolinecarboxylic acid, 1-cyclopropyl-6,8-difluoro-1,4-dihydro-4-oxo-7-(3-isobutyl-1-pipereazinyl)-3-quinolinecarboxylic acid, 1-cyclopropyl-6,8-difluoro-1,4-dihydro-4-oxo-(3-methyl-4-n-propyl-1-piperazinyl)-3-quinolinecarboxylic acid, 1-cyclopropyl-6,8-difluoro-1,4-dihydro-4-oxo-7-(3-methyl-4-isopropyl)-1-piperazinyl)-3-quinolinecarboxylic acid, 1-cyclopropyl-6,8-difluoro-1,4-dihydro-4-oxo-7-(4-n-butyl-3-methyl-1-piperazinyl)-3-quinolinecarboxylic acid and 1-cyclopropyl-6,8-difluoro-1,4-dihydro-4-oxo-7-morpholinyl-3-quinolinecarboxylic acid, and their pharmaceutically usable acid addition salts, alkali metal salts, alkaline earth metal salts or hydrates.

Finally, ciprofloxacin or enrofloxacin are also particularly preferably employed as the active compound in the formulations according to the invention.

In addition to water for injection purposes, aqueous suspensions for intramuscular injection can furthermore also contain as the liquid excipient, for example, ethanol, glycerol, propylene glycol, polyethylene glycol and triethylene glycol. Various substances such as phosphate, citrate, tris, ascorbate, acetate, succinate, tartrate, gluconate and lactate buffers can be used for adjusting the pH as far as possible to within the physiological range of about pH 7.4 or for buffering. The pH of the aqueous formulations according to the invention is 4.5–8.5, preferably 6.5–7.5. The osmolality of the aqueous suspensions is 200-900 m osmol/kg, preferably 260-390 m osmol/kg, and can be adjusted to suit isotonic conditions by additions of NaCl, glucose, fructose, glycerol, sorbitol, mannitol, sucrose or xylitol or mixtures of these substances.

It is moreover possible to use other formulating agents, such as thickeners (for example methylcellulose, hydroxyethylcellulose, hydroxypropylcellulose, sodium carboxymethylcellulose, polyvinylpyrrolidone, gelatine and the like), absorption agents, light screens, absorption inhibitors, crystallization retarders, complexing agents (for example NaEDTA, phosphates, nitrates, acetates, citrates and others), antioxidants (ascorbic acid, sulphite compounds, L-cysteine, thiodipropionic acid, thiolactic acid, monothioglycerol, propyl gallate and others) and preservatives (PHB esters, phenol and derivatives, organomercury compounds, chlorobutanol, benzyl alcohol, ethanol, 1,3-butanediol, benzalkonium chloride, chlorhexidine salts, benzoic acid and salts, sorbic acid and others). Local anaesthetics, such as, for example, procaine HCl, lidocaine HCl and others, can be added to the aqueous suspensions if appropriate.

When preparing the aqueous suspensions, it must be ensured that the particle size is 0.5–50 μm, in particular 4–40 μm. Control of the release of active compound from the intramuscular suspension depot can be achieved by controlled mixing of different particle size classes of the active substance.

In the case of aqueous suspensions, the particle sizes of 90% of the particles are preferably 10–20 μm. The viscosity of the aqueous suspensions is 5–500 mPa.s, preferably 10–130 mPa.s.

Aqueous suspensions of gyrase inhibitors can be prepared in various ways. On the one hand, the active compounds from the gyrase inhibitor class can be incorporated in micronized form into the aqueous excipient medium, the auxiliaries mentioned being included; in this procedure, it should strictly be ensured that no crystal growth occurs beyond the limits mentioned. If appropriate, the active compound must be prepared in the form of one of its stable hydrate stages and further processed to a suspension. If final sterilization by heat is not possible, manufacture must be carried out under aseptic conditions using pretreated active compounds and auxiliaries. Final sterilization, as by radiation is possible.

Aqueous suspensions of gyrase inhibitors of the quinolone type can moreover be prepared by controlled precipitation from a solution; there is the possibility, for example, of dissolving the active compound in a physiologically tolerated acid from the group consisting of hydrochloric acid, methanesulphonic acid, propionic acid, succinic acid, glutaric acid, citric acid, fumaric acid, maleic acid, tartaric acid, glutamic acid, gluconic acid, glucuronic acid, galacturonic acid, ascorbic acid, phosphoric acid, adipic acid, hydroxyacetic acid, sulphuric acid, nitric acid, acetic acid, malic acid, L-aspartic acid, lactic acid, isethionic acid, lactobionic acid and oxatic acid or in amino acids from the group consisting of L-Arginine, L-Aspartic, L-Cysteic, L-Glutamic, Glycine, L-Leucine, L-Lysine and L-Serine, if appropriate while warming slightly, preferably to 20°–80° C.

An excess of acid is preferably used, for example in accordance with the doctrine of European Patent Applications 86 114 131.5 and 84 110 474.8. The acid solution is then adjusted to the physiological pH of 7 by addition of a physiologically tolerated alkaline solution, for example of sodium hydroxide, potassium hydroxide or meglumine, the active compound being precipitated out of the solution in finely divided form. On the other hand, there is also the possibility of dissolving the active compound of the quinolone/naphthyridone gyrase inhibitor type in an alkaline medium using one of the bases mentioned and then to precipitate it by one of the acids mentioned.

However, the acids and alkaline solutions can be combined without using pressure, but also with pressure, in a range from 2 to 100 bar, it being possible to control the resulting particle size in the suspension via the preparation conditions defined. The actual precipitation operation can also be followed by additional homogenization using high-speed stirrers, rotor-stator homogenizers, high pressure homogenizers (100–1000 bar) and similar methods. If final sterilization is prohibited because of possible particle growth, the suspension is to be prepared under aseptic conditions by combining sterilized and sterile-filtered acid and basic part components with one another under strictly aseptic conditions. If appropriate, one of the preservatives mentioned or a combination thereof can be employed in a suitable dosage in order to guarantee a germ-free preparation. Final sterilization in form of a γ-ray sterilization may be applied too.

A presentation form which contains the active compound in a dry form without a liquid excipient can moreover be provided. The separate liquid excipient is combined with the solids content of the recipe only shortly before administration, in which case homogeneous distribution of the solids particles in the liquid phase must be guaranteed by brief shaking.

Under the provisions set forth hereinabove and hereinbelow there are particularly preferred oil based intramuscular injection formulations which contain the active compound in water-soluble, crystalline or amorphous form, for instance in form of the hydrochloride, lactate, mesilate, p-tolyl sulphonate or other salts produced with physiologically well-tolerated acids as well as which contain interfacially active substances, as for instance lecithin in the form of soy bean lecithin, egg lecithin, brain lecithin or rape lecithin or other physiologically well-tolerated tensides in concentrations of 0.1 to 30%, particularly 0.2 to 10%, above all 0.5 to 5.0% W/V as well as which contain, in addition to the water-soluble active compound in the form of their salts, an excess of physiologically well-tolerated acids, as for instance lactic acid or citric acid in the range of 1 to 300 mmol/l, particularly 5 to 50 mmol/l, preferably 10 to 30 mmol/l.

Oily suspensions of quinolone-type gyrase inhibitors contain the active compound either in the form of the betaine or in the form of water-soluble salts. Physiologically well-tolerated acids appropriate for formation of salts are set forth hereinabove.

Oily suspensions can contain, as non-aqueous excipients, for example almond oil, arachis oil, olive oil, poppyseed oil, sesame oil, cottonseed oil, soya bean oil, corn oil, castor oil, ethyl oleate, oleyl oleate, isopropyl myristate, isopropyl palmitate, medium-chain triglycerides and others. Ethanol, glycerol, propylene glycol, polyethylene gLycoL, 1.3-butane diol, benzyl alcohol, diethylene glycol and triethylene glycol of various origins, polyoxyethylene-polyoxypropylene copolymers of the Pluronic ® type, polyoxysorbitan fatty acid esters, sorbitan fatty acid esters monoolein, cremophor EL ®, Inwitor 742 ® and different types of lecithin such as soy bean lecithin, egg lecithin, brain lecithin and rape lecithin can be used as further auxiliaries which can be combined with the substances mentioned.

Antioxidants which are used are α-, β-, γ- and δ-tocopherol, ascorbyl palmitate, ascorbyl stearate, L-cysteine, thiodipropionic acid, thiolactic acid, thioglycolic acid, monothioglycerol, propyl gallate, butylhydroxyanisole, butylhydroxytoluene and others.

If appropriate, a desired viscosity can be brought about by diluents such as ethanol or benzyl alcohol and by thickeners such as aluminum stearate. Acids such as those mentioned hereinabove may be added as absorption enhancers. Viscosity values for oily suspensions are 5–500 mPa.s, preferably 10–150 mPa.s.

Oily suspensions are prepared by combining the oily excipient with the auxiliaries contained therein and the active compound, which has been comminuted to the desired particle size, using suitable apparatuses (see above) and homogenizing the mixture. The particle sizes of 90% of the particles are 0.5–150 μm, preferably 4–12 μm. If final sterilization in the release vessel is prohibited because of a possible change in the particle size of the active compound, the suspension must again be prepared under aseptic conditions. Sterile filtration of the oily phase containing suitable auxiliaries in dissolved form is also indicated, such as antimicrobial pretreatment of the active compound, for example by heat treatment. Final sterilization in the form of a γ-ray sterilization may also be applied.

In addition to a finished suspension, a formulation which is to be freshly prepared shortly before administration can also be provided. In this case, the active compound must be homogeneously suspendable in the liquid excipient within a short time by shaking the vessel containing the formulation.

The invention also relates to suspension concentrates which are converted into the formulations according to the invention shortly before administration.

These concentrates can have various compositions. This invention relates to all the further combinations of concentrates and/or suspensions and solvents or solutions required for dilution which lead to the suspensions according to the invention.

This invention also relates to other presentation forms or combinations of presentation forms which in the end lead to the injection solutions according to the invention—regardless of the procedure.

The containers filled with suspensions, active compound, solvents and other presentation forms, such as suspension concentrates, can be made of glass or of plastic. The container materials here can contain substances which impart special protection to the contents, such as, for example, protection from light or protection from oxygen. In addition to small volume vessels, from which the suspension must be drawn into the injection syringe before administration, the vessels here can also be finished injection systems.

The injection formulations according to the invention are used in the therapeutic treatment of the human or animal body.

The formulations according to the invention have a low toxicity and exhibit a broad antibacterial spectrum against Gram-positive and Gram-negative germs, in particular against Enterobacteriaceae; above all also against those which are resistant towards various antibiotics, such as, for example, penicillins, cephalosporins, aminoglycosides, sulphonamides and tetracyclines.

The formulations according to the invention are active against a very broad spectrum of microorganisms. Gram-negative and Gram-positive bacteria and bacteria-like microorganisms can be combated and the diseases caused by these pathogens can be prevented, alleviated and/or cured with the aid of these formulations.

The formulations according to the invention are particularly active against bacteria and bacteria-like microorganisms. They are therefore particularly suitable for the prophylaxis and chemotherapy, in human and veterinary medicine, of local and systemic infections caused by these pathogens.

For example, it is possible to treat and/or prevent local and/or systemic diseases caused by the following pathogens or by mixtures of the following pathogens: Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative cocci (*Neisseria gonorrhoeae*) and Gram-negative rod-shaped bacilli, such as Enterobacteriaceae, for example *Escherichia coli, Haemophilus influenzae,* Citrobacter (*Citrob. freundii* and *Citrob. divernis*), Salmonella and Shigella; and furthermore Klebsiellae (*Klebs. pneumoniae, Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia and Yersinia, and the genus Acinetobacter. The antibacterial spectrum moreover includes the genus Pseudomonas (*Ps. aeruginosa* and *Ps. maltophilia*) and strictly anaerobic bacteria, such as, for example, *Bacteroides fragilis,* representatives of the genus Peptococcus and Peptostreptococcus and the genus Clostridium; and furthermore Mykoplasma (*M. pneumoniae, M. hominis* and *M. urealyticum*) and Mycobacteria, for example *Mycobacterium tuberculosis.*

The above list of pathogens is to be interpreted merely by way of example and in no way as limiting. Examples which may be mentioned of diseases which can be caused by the pathogens or mixed infections mentioned and can be prevented, alleviated or cured by the compounds according to the invention are: infection diseases in humans, such as, for example, otitis, pharyngitis, pneumonia, peritonitis, pyelonephritis, cystitis, endocarditis, systemic infections, bronchitis (acute and chronic), septic infections, diseases of the upper respiratory tract, diffuse panbronchiolitis, pulmonary emphysema, dysentery, enteritis, liver abscesses, urethritis, prostatitis, epididymitis, gastrointestinal infections, bone and joint infections, cystic fibrosis, skin infections, postoperative wound infections, abscesses, phlegmons, wound infections, infected burns, burn wounds, infections in the oral region, infections following dental operations, osteomyelitis, septic arthritis, cholecystitis, peritonitis with appendicitis, cholangitis, intraabdominal abscesses, pancreatitis, sinusitis, mastoiditis, mastitis, tonsillitis, typhoid, meningitis and infections of the nervous system, salpingitis, endometritis, genital infections, pelveoperitonitis and eye infections.

Bacterial infections can also be treated in other species as well as in humans. Examples which may be mentioned are:

pigs: colidiarrhoea, enterotoxaemia, sepsis, dysentery, salmonellosis, mastitis-metritis agalactia syndrome and mastitis;

ruminants (cattle, sheep, goats): diarrhoea, sepsis, bronchopneumonia, salmonellosis, pasteurellosis, mycoplasmosis and genital infections;

horses: bronchopneumonia, joint ill, puerperal and postpuerperal infections and salmonellosis;

dogs and cats: bronchopneumonia, diarrhoea, dermatitis, otitis, urinary tract infections and prostatitis;

poultry (chickens, turkeys, quails, pigeons, ornamental birds and others): mycoplasmosis, *E. coli* infections, chronic diseases of the respiratory tract, salmonellosis, pasteurellosis and psittacosis.

Bacterial diseases can also be treated in the rearing and keeping of stock and ornamental fish, the antibacterial spectrum extending beyond the abovementioned pathogens to further pathogens, such as, for example, Pasteurella, Brucella, Campylobacter, Listeria, Erysipelothrix, Corynebacteria, Borrelia, Treponema, Nocardia, Rickettsia and Yersinia.

The auxiliaries mentioned in the examples are commercially available and are defined in part in H. P. Fiedler, Lexikon der Hilfsstoffe für Pharmazie, Kosmetik und angrenzende Gebiete (Dictionary of Auxiliaries for Pharmacy, Cosmetics and Related Areas), Editio Cantor KG - Aulendorf i. Württ. 1971 (for example Tween ® and Miglyol ®).

The invention will be further described with reference to the accompanying drawings relating to comparison experiments which demonstrate the good tolerability of a ciprofloxacin intramuscular suspension in contrast to ciprofloxacin intramuscular solutions.

Figure 1:
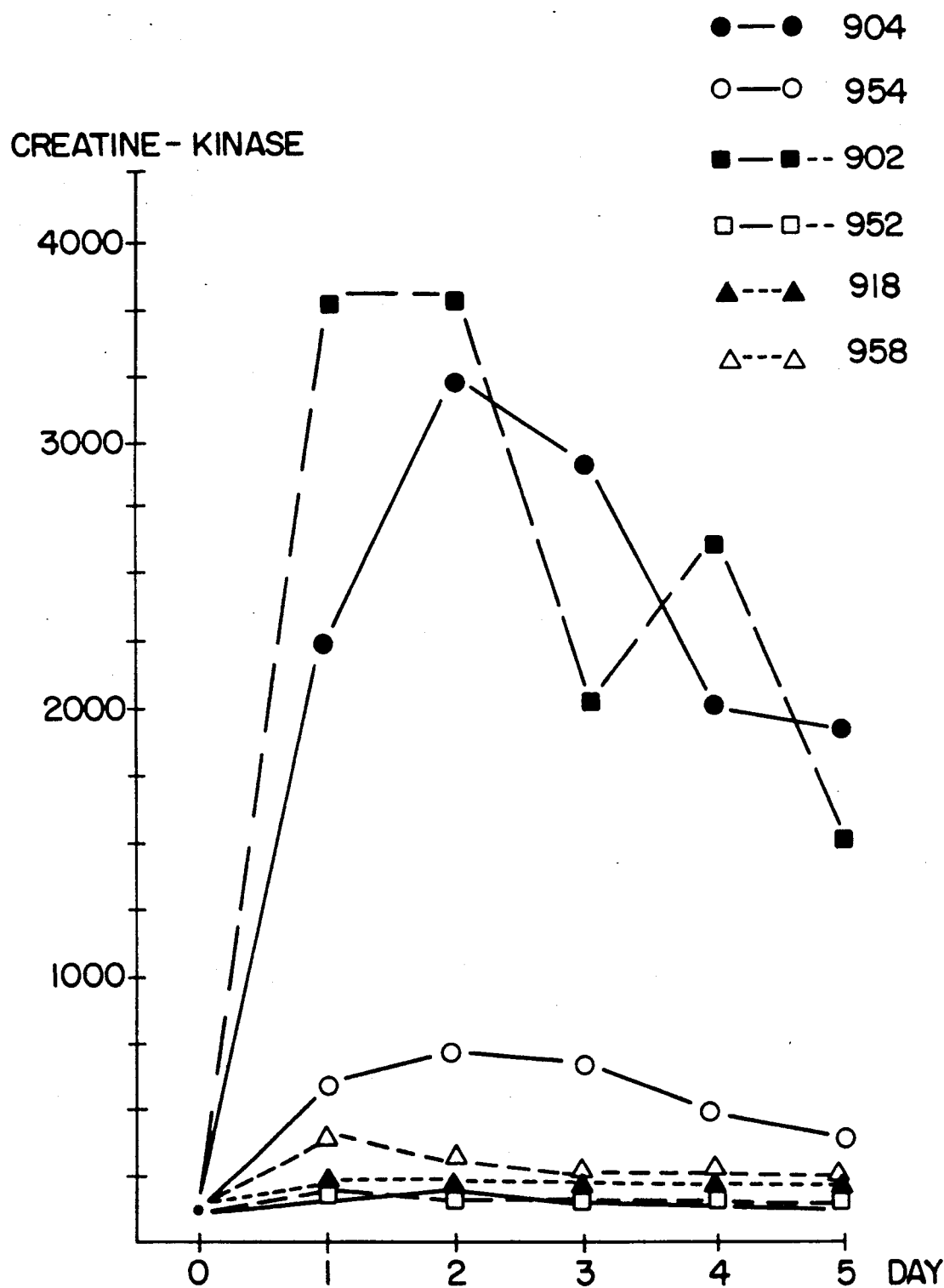
FIG. 1 shows the course of the creatinine kinase following intramuscular administration of ciprofloxacin intramuscular solutions, an intramuscular suspension and comparison solutions.
Figure 2:
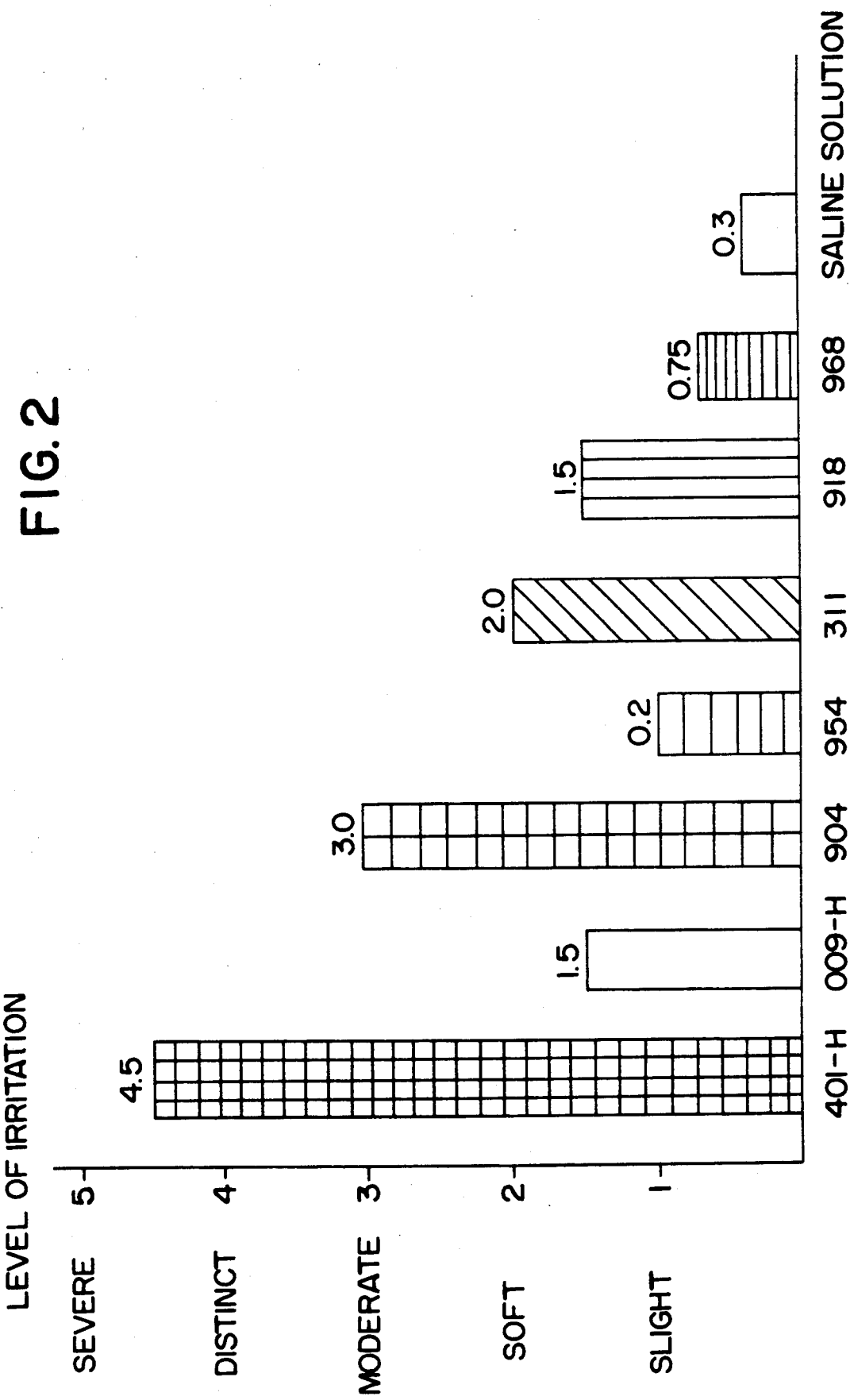
FIG. 2 shows the local irritation following intramuscular administration of ciprofloxacin solutions and a ciprofloxacin intramuscular suspension and comparison solutions.
Figure 3:
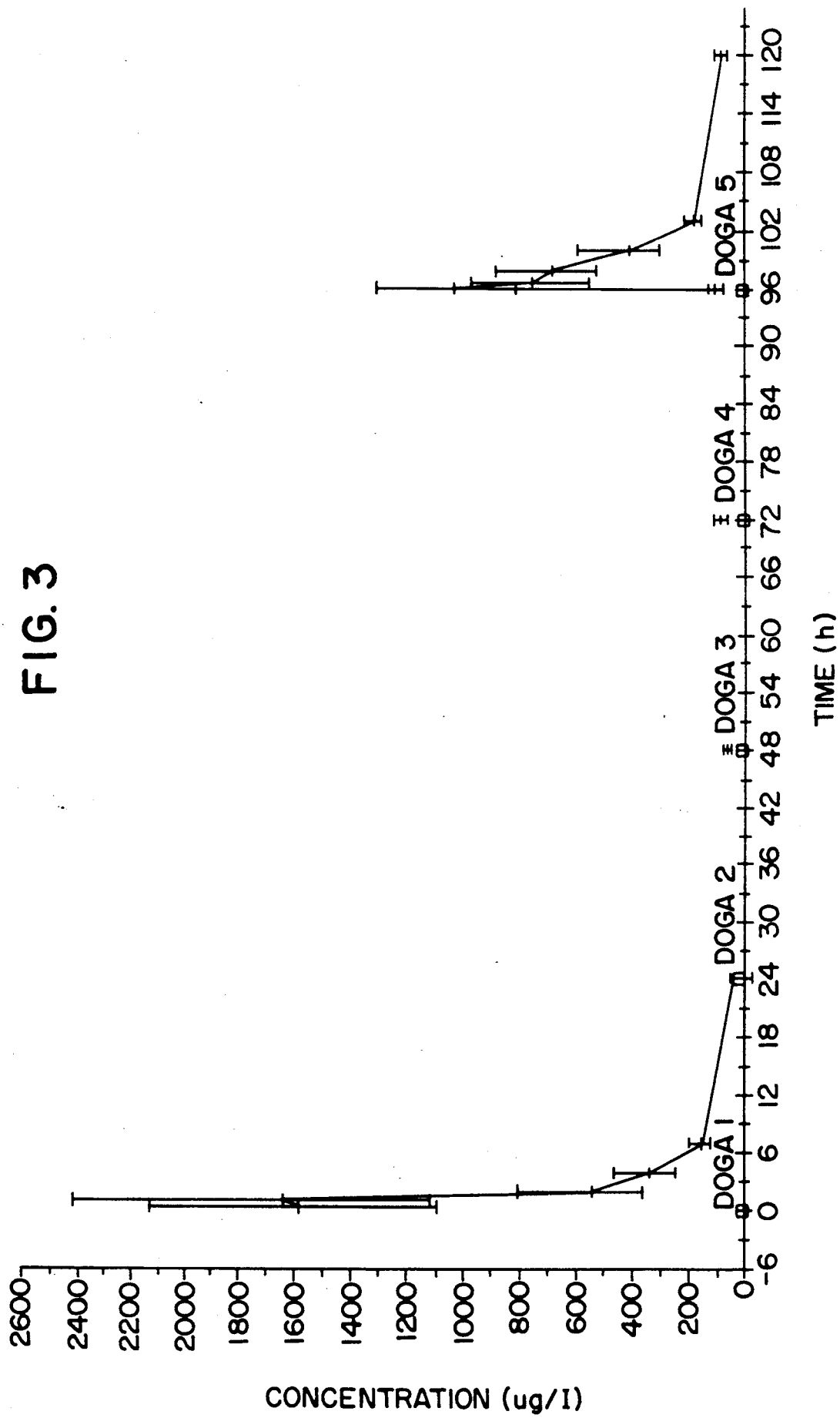
FIG. 3 shows the blood plasma levels after application of an oily ciprofloxacin-HCl suspension to rabbits.

The very fast absorption of Ciprofloxacin-HCl from an oily suspension into the blood is clearly evident.

Results

1) The local irritations following intramuscular administration of 5% weight/volume ciprofloxacin suspensions are clearly less than those caused by intramuscular solutions (Rabbit test)

2) In contrast to the intramuscular solutions tested, administration of the ciprofloxacin suspension causes no increase in the serum creatinine kinase.

The formulations used for the experiments are described below (rabbit test).

| Ciprofloxacin intramuscular injection solution 5% w/v A | |
|---|---|
| Ciprofloxacin | 50.0 g |
| Lactic acid saponified 20% | 131.0 g |
| Water for injection purposes | 840.6 g |
| | 1021.6 g | clear yellowish solution; pH 3.9, isotonic

| Ciprofloxacin intramuscular injection solution 5% weight/volume 2 ml B | |
|---|---|
| Ciprofloxacin | 50.0 g |
| 100% strength acetic acid | 25.0 g |
| Water for injection purposes | 943.7 g |
| | 1,018.7 g (1 l) | clear, yellow solution; pH 4.2

| Ciprofloxacin intramuscular injection solution 5% weight/volume 2 ml C | |
|---|---|
| Ciprofloxacin | 50.0 g |
| Methanesulphonic acid | 14.5 g |
| Anhydrous glycerol | 12.5 g |
| 0.1 N NaOH solution | to pH 4.2 |
| Water for injection purposes | 945.5 g |
| | 1,022.5 g (1 l) |

Clear, yellow solution; pH 4.2

| Ciprofloxacin intramuscular suspension 5% weight/volume 2 ml D | |
|---|---|
| Ciprofloxacin | 50.0 g |
| 20% weight/weight NaOH solution | 55.2 g |
| Citric acid fine grit | 17.9 g |
| Tylopur C 300 P | 2.0 g |
| Water for injection purposes | 907.3 g |
| | 1,032.4 g (1 l) |

Sedimenting, reshakable suspensions of pH 7; particle size of the crystals predominantly less than 10 μm.

| Ciprofloxacin suspension 5% w/v E | |
|---|---|
| Ciprofloxacin-HCl | 58.2 g |
| Phospholipon 100 | 5.0 g |
| Benzyl alcohol distilled | 20.0 g |
| Miglyol 812 ® | 883.8 g |
| | 967.0 g | white oily suspension;

| Ciprofloxacin placebo F | |
|---|---|
| Lactic acid saponified 20% | 64.06 g |
| 2 N NaOH - solution | 38.4 g |
| Sodium chloride | 1.46 g |
| Water for injection purposes | 900.08 g |
| | 1004.0 g | clear colorless solution isotonic; pH 3.9

| Ciprofloxacin placebo Ciprofloxacin intramuscular injection solution placebo 5% weight/volume 2 ml G | |
|---|---|
| 100% strength acetic acid | 50.0 g |
| 1 N NaOH solution | to pH 4.2 |
| Water for injection purposes | 956.7 g |
| | 1,006.7 g |

Clear, colorless solution; pH about 4.2

| Ciprofloxacin placebo Ciprofloxacin intramuscular injection solution placebo 5% weight/volume 2 ml H | |
|---|---|
| Methanesulphonic acid | 14.5 g |
| Anhydrous glycerol | 12.5 g |
| 1 N NaOH solution | about 158.06 g |
| Water for injection purposes | 825.54 g |
| | 1,010.6 g |

Clear, almost colorless solution; pH about 4.2
Osmolality about 425 m osmol

| Ciprofloxacin placebo Ciprofloxacin intramuscular injection solution placebo 5% weight/volume 2 ml J | |
|---|---|
| Citric acid fine grit | 17.9 g |
| 20% weight/weight NaOH solution | 55.6 g |
| Tylopur C 300 P ® | 2.0 g |
| Water for injection purposes | 940.3 g |
| | 1,015.8 g (1 l) |

Colorless, slightly opalescent solution; pH 6.8

Examples

1.

| Ciprofloxacin | 50 g | preparation by |
| 20% weight/weight NaOH solution | 55.2 g | precipitation |
| Citric acid | 17.9 g | |
| Tylopur C 300 P ® | — | |
| Water | 909.3 g | pH = 6.5 |

2.

| Ciprofloxacin | 50 g | preparation by |
| 20% weight/weight NaOH solution | 55.2 g | precipitation |
| Citric acid | 17.9 g | |
| Tylopur C 300 P ® | 2.0 g | |
| Water | 907.3 g | pH = 6.7 |

3.

-continued

| | | |
|---|---|---|
| Ciprofloxacin | 50 g | preparation by precipitation |
| 20% weight/weight NaOH solution | 55.2 g | |
| Citric acid | 17.9 g | |
| Tylopur C 300 P ® | 5.0 g | |
| Water | 904.3 g | pH = 6.5 |

4.

| | | |
|---|---|---|
| Ciprofloxacin | 50 g | preparation by precipitation |
| 20% weight/weight NaOH solution | 55.2 g | |
| Citric acid | 17.9 g | |
| Tylopur C 300 P ® | 7.5 g | |
| Water | 901.8 g | pH = 6.5 |

5.

| | | |
|---|---|---|
| Ciprofloxacin | 50 g | preparation by precipitation |
| 20% weight/weight NaOH solution | 55.2 g | |
| Citric acid | 17.9 g | |
| Tylopur C 300 P ® | 7.5 g | |
| Water | 899.5 g | pH = 6.5 |

6.

| | | |
|---|---|---|
| Ciprofloxacin | 50 g | preparation by precipitation |
| 20% weight/weight NaOH solution | 55.2 g | |
| Citric acid | 16.0 g | |
| Tylopur C 300 P ® | 2.0 g | |
| Water | 909.2 g | pH = 7.9 |

7.

| | | |
|---|---|---|
| Ciprofloxacin | 50 g | preparation by precipitation |
| 20% weight/weight NaOH solution | 55.2 g | |
| Citric acid | 24.7 g | |
| Tylopur C 300 P ® | 2.0 g | |
| Water | 900.5 g | pH = 5.3 |

8.

| | | |
|---|---|---|
| Ciprofloxacin | 50 g | preparation by precipitation |
| 20% weight/weight NaOH solution | 55.2 g | |
| Citric acid | 17.9 g | |
| Tylopur C 300 P ® | 2.0 g | |
| Tween 20 | 2.0 g | |
| Water | 900.5 g | pH = 6.9 |

9.

| | | |
|---|---|---|
| Ciprofloxacin | 5.0 g | preparation by precipitation |
| 20% weight/weight NaOH solution | 9.43 g | |
| Lipoid E 80 | 0.2 g | |
| Citric acid | 1.8 g | |
| Tylopur C 300 P ® | 0.2 g | |
| Water | 77.17 g | |

10.

| | | |
|---|---|---|
| Ciprofloxacin | 50.0 g | preparation by precipitation |
| 20% weight/weight NaOH solution | 55.2 g | |
| Methanesulphonic acid | 16.15 g | |
| 10% weight/weight NaOH solution | 18.83 ml | |
| Water | 400.8 g | pH = 7.0 |

11.

| | | |
|---|---|---|
| Ciprofloxacin | 50.0 g | preparation by precipitation |
| Methanesulphonic acid | 16.15 g | |
| L-Arginine | 6.113 g | |
| Water | 407.33 g | pH = 7.0 |

12.

| | | |
|---|---|---|
| Ciprofloxacin | 50.0 g | preparation by precipitation |
| Methanesulphonic acid | 16.15 g | |
| Trimethanol (tris) | 4.41 g | |
| Water | 408.37 g | pH = 7.0 |

13.

| | | |
|---|---|---|
| Micronized ciprofloxacin hydrate (85.5%) | 5.85 g | Suspension of micronized ciprofloxacin hydrate in the aqueous phase |
| Tylopur C 300 P ® | 0.2 g | |
| Anhydrous glycerol | 2.5 g | |
| Water | to 100 ml | |

14.

| | | |
|---|---|---|
| Micronized ciprofloxacin hydrate (85.5%) | 5.85 g | Suspension of micronized ciprofloxacin hydrate in the |
| Tylopur C 300 P ® | 0.2 g | |
| Anhydrous glycerol | 2.5 g | |

-continued

| | | |
|---|---|---|
| Water | to 100 ml | aqueous phase |

15.

| | | |
|---|---|---|
| Micronized ciprofloxacin hydrate (85.5%) | 5.85 g | Suspension of micronized ciprofloxacin hydrate in the aqueous phase pH 6.8 |
| Tylopur C 300 P ® | 0.75 g | |
| Tween 80 ® | 0.2 g | |
| Anhydrous glycerol | 2.5 g | |
| Water | to 100 ml | |

16.

| | | |
|---|---|---|
| Micronized ciprofloxacin hydrate (85.5%) | 5.85 g | Suspension of micronized ciprofloxacin hydrate in the aqueous phase pH 6.8 |
| Tylopur C 300 P ® | 0.75 g | |
| Lipoid E 80 ® | 0.2 g | |
| Anhydrous glycerol | 2.5 g | |
| Water | to 1,000 ml | |

17.

| | | |
|---|---|---|
| Micronized ciprofloxacin hydrate (85.5%) | 5.85 g | Suspension of micronized ciprofloxacin hydrate in the aqueous phase pH 6.8 |
| Tylopur C 300 P ® | 0.2 g | |
| Tween 80 ® | 0.2 g | |
| Anhydrous glycerol | 2.5 g | |
| Water | to 100 ml | |

18.

| | | |
|---|---|---|
| Micronized ciprofloxacin hydrate (85.5%) | 5.85 g | Suspension of micronized ciprofloxacin hydrate in the aqueous phase pH 6.8 |
| Tylopur C 300 P ® | 0.2 g | |
| Lipoid E 80 ® | 0.2 g | |
| Anhydrous glycerol | 2.5 g | |
| Water | to 1,000 ml | |

19.

| | | |
|---|---|---|
| Ciprofloxacin hydrate (85.5%) | 5.85 g | Suspension of micronized ciprofloxacin hydrate in the aqueous phase pH 7 |
| Tylopur C 300 P ® | 0.2 g | |
| Lipoid E 80 | 0.2 g | |
| Water | 90.0 ml | |

20.

| | | |
|---|---|---|
| Ciprofloxacin hydrate (85.5%) | 5.85 g | Suspension of micronized ciprofloxacin hydrate in the aqueous phase pH 7 |
| Tylopur C 300 P ® | 0.2 g | |
| Citrate buffer solution pH 7 | 90.0 g | |
| Lipoid E 80 | 0.2 g | |

21.

| | | |
|---|---|---|
| Ciprofloxacin hydrate (85.5%) | 5.85 g | Suspension of micronized ciprofloxacin hydrate in the aqueous phase pH 7 |
| Tylopur C 300 P ® | 0.2 g | |
| Phosphate buffer solution pH 7 | 90.0 g | |
| Lipoid E 80 | 0.2 ml | |

22.

| | | |
|---|---|---|
| Ciprofloxacin | 5.0 g | preparation of precipitation |
| 20% weight/weight NaOH solution | 3.27 g | |
| 85% strength H$_3$PO$_4$ solution | 1.07 g | |
| Tylopur C 300 P ® | 0.2 g | |
| Water | 93.14 g | |

23.

| | | |
|---|---|---|
| Ciprofloxacin | 50.0 g | pH/osmolality: 285 m osmol/kg |
| 20% weight/weight NaOH solution | 55.57 g | |
| Citric acid fine grit | 17.9 g | |
| Water | 903.6 g | |

Particle size <10 μm
Precipitation under aseptic conditions via a reaction jet 60/40 bar and high pressure homogenization under 400 bar.

24.

| | | |
|---|---|---|
| Ciprofloxacin | 100.0 g | |
| 20% weight/weight NaOH solution | 62.0 g | |
| Citric acid fine grit | 19.8 g | |
| Water | 869.2 g | pH 7.0 |

Particle size <2-5 μm (90% less than 10 μm)
Precipitation under aseptic conditions via a reaction jet 60/40 bar and high pressure homogenization under 400 bar.

25.

| | | |
|---|---|---|
| Ciprofloxacin | 100.0 g | |
| 20% weight/weight NaOH solution | 62.0 g | |

| | | |
|---|---|---|
| Citric acid fine grit | 19.8 g | |
| Tween 80 ® | 0.1 g | |
| Water | 869.2 g | pH 7.0 |

26.

| | | |
|---|---|---|
| Ciprofloxacin | 100.0 g | |
| 20% weight/weight NaOH solution | 62.0 g | |
| Citric acid fine grit | 19.8 g | |
| Tween 80 ® | 1.0 g | |
| Water | 868.2 g | pH 7.0 |

27.

| | | |
|---|---|---|
| Ciprofloxacin | 100.0 g | |
| 20% weight/weight NaOH solution | 62.0 g | |
| Citric acid fine grit | 19.8 g | |
| Tween 80 ® | 2.0 g | |
| Water | 867.1 g | pH 7.0 |

28.

| | | |
|---|---|---|
| Ciprofloxacin | 100.0 g | |
| 20% weight/weight NaOH solution | 62.0 g | |
| Citric acid fine grit | 19.8 g | |
| Tween 80 ® | 2.0 g | |
| Water | 867.1 g | pH 7.0 |

29.

| | | |
|---|---|---|
| Ciprofloxacin | 40.0 g | preparation by precipitation |
| 20% weight/weight NaOH solution | 24.8 g | |
| Citric acid fine grit | 7.92 g | |
| Lipoid E 75 ® | 4.0 g | |
| Water | 343.6 g | pH 7.0 |

30.

| | | |
|---|---|---|
| Ciprofloxacin | 200.0 g | preparation by precipitation |
| 20% weight/weight NaOH solution | 62.8 g | |
| Citric acid fine grit | 41.88 g | |
| Water | 738.27 g | pH 7.05 |

31.

| | | |
|---|---|---|
| Ciprofloxacin | 20.0 g | preparation by precipitation |
| 20% weight/weight NaOH solution | 12.4 g | |
| 15% weight/weight H$_3$PO$_4$ solution | 21.38 ml | |
| Water | to 100 ml | pH 7.05 |

32.

| | | |
|---|---|---|
| Ciprofloxacin | 15.0 g | preparation by precipitation |
| 20% weight/weight NaOH solution | 9.3 g | |
| 15% weight/weight H$_3$PO$_4$ solution | 16.05 ml | |
| Water | to 100 ml | |

33.

| | | |
|---|---|---|
| Ciprofloxacin | 25.0 g | preparation by precipitation |
| 20% weight/weight NaOH solution | 11.25 g | |
| 20% weight/weight lactic acid solution | 3.72 g | |
| 15% weight/weight H$_3$PO$_4$ solution | 21.5 ml | |
| Water | to 100 ml | pH 7.0 |

34.

| | | |
|---|---|---|
| Ciprofloxacin | 20.0 g | preparation by precipitation |
| 20% weight/weight NaOH solution | 10.0 g | |
| 20% weight/weight lactic acid solution | 7.44 g | |
| 15% weight/weight H$_3$PO$_4$ solution | 12.0 ml | |
| Water | to 100 ml | pH 7.0 |

35.

| | | |
|---|---|---|
| Ciprofloxacin | 20.0 g | preparation by precipitation |
| 20% weight/weight NaOH solution | 8.75 g | |
| 20% weight/weight lactic acid solution | 11.16 g | |
| 15% weight/weight H$_3$PO$_4$ solution | 6.7 ml | |
| Water | to 100 ml | pH 7.0 |

36.

| | | |
|---|---|---|
| Ciprofloxacin | 20.0 g | preparation by precipitation |
| 20% weight/weight NaOH solution | 12.4 g | |
| 15% weight/weight H$_3$PO$_4$ solution | 21.1 ml | |
| Tylopur C 300 P ® | 0.05 g | |
| Water | to 100 ml | pH 7.0 |

37.

| | | |
|---|---|---|
| Ciprofloxacin | 20.0 g | preparation by precipitation |
| 20% weight/weight NaOH solution | 12.4 g | |
| 15% weight/weight H$_3$PO$_4$ solution | 21.1 ml | |
| HPC | 0.05 g | |
| Water | to 100 ml | pH 7.0 |

38.

| | | |
|---|---|---|
| Ciprofloxacin | 20.0 g | preparation by precipitation |
| 20% weight/weight NaOH solution | 12.4 g | |
| 15% weight/weight H$_3$PO$_4$ solution | 21.1 ml | |
| Tween 80 ® | 0.05 g | |
| Water | to 100 ml | pH 7.0 |

39.

| | | |
|---|---|---|
| Ciprofloxacin | 20.0 g | preparation by precipitation |
| 20% weight/weight NaOH solution | 12.4 g | |
| 15% weight/weight H$_3$PO$_4$ solution | 21.1 ml | |
| Tween 80 ® | 1.0 g | |
| Water | to 100 ml | pH 7.0 |

40.

| | | |
|---|---|---|
| Ciprofloxacin hydrochloride | 5 g | Suspension of ciprofloxacin hydrochloride |
| Ethyl oleate | 50 g | |

41.

| | | |
|---|---|---|
| Ciprofloxacin hydrochloride | 10 g | |
| Ethyl oleate | 50 g | |

42.

| | | |
|---|---|---|
| Ciprofloxacin hydrochloride | 30 g | |
| Ethyl oleate | 50 g | |

43.

| | | |
|---|---|---|
| Ciprofloxacin hydrochloride | 25 g | |
| Ethyl oleate | 50 g | |

44.

| | | |
|---|---|---|
| Ciprofloxacin hydrochloride | 5 g | |
| Miglyol 812 ® | 50 g | |

45.

| | | |
|---|---|---|
| Ciprofloxacin hydrochloride | 10 g | |
| Miglyol 812 ® | 50 g | |

46.

| | | |
|---|---|---|
| Ciprofloxacin hydrochloride | 15 g | |
| Miglyol 812 ® | 50 g | |

47.

| | | |
|---|---|---|
| Ciprofloxacin hydrochloride | 5 g | |
| Peanut oil | 50 g | |

48.

| | | |
|---|---|---|
| Ciprofloxacin hydrochloride | 5 g | |
| Ethyl oleate/Phospholipon 100 ® = 99.5/0.5 | 50 g | |

49.

| | | |
|---|---|---|
| Ciprofloxacin hydrochloride | 30 g | |
| Ethyl oleate/Phospholipon 100 ® = 99.5/0.5 | 50 g | |

50.

| | | |
|---|---|---|
| Ciprofloxacin hydrochloride | 10 g | |
| Miglyol 812 ®/Phospholipon 100 ® = 99.5/0.5 | 50 g | |

51.

| | | |
|---|---|---|
| Ciprofloxacin hydrochloride | 15 g | |
| Miglyol 812 ®/Phospholipon 100 ® = 99.5/0.5 | 50 g | |

52.

| | | |
|---|---|---|
| Ciprofloxacin | 30 g | |
| Ethyl oleat ® | 50 g | |

53.

| | | |
|---|---|---|
| Ciprofloxacin | 10 g | |
| Miglyol 812 ® | 50 g | |

-continued

54.
| | | |
|---|---|---|
| Ciprofloxacin | 2.5 g | |
| Peanut oil | 50 g | |

55.
| | | |
|---|---|---|
| Ciprofloxacin hydrochloride | 30 g | |
| Ethyl oleate | 50 g | |
| Ascorbyl palmitate | 0.1 g | |
| Lecithin (Phospholipon 100) ® | 0.5 g | |

56.
| | | |
|---|---|---|
| Ciprofloxacin hydrochloride | 25 g | |
| Miglyol 812 ® | 50 g | |
| Ascorbyl palmitate | 0.1 g | |
| Lecithin (Phospholipon 100) ® | 0.5 g | |

57.
| | | |
|---|---|---|
| Ciprofloxacin hydrochloride | 30 g | |
| Ethyl oleate | 50 g | |
| Ascorbyl palmitate | 0.1 g | |
| Lecithin (Phospholipon 100) ® | 0.5 g | |
| Benzyl alcohol | 3 g | |

58.
| | | |
|---|---|---|
| Ciprofloxacin hydrochloride | 25 g | |
| Miglyol 812 ® | 50 g | |
| Benzyl alcohol | 3 g | |
| Lecithin (Phospholipon 100) ® | 0.5 g | |
| Ascorbyl palmitate | 0.1 g | |

59.
| | | |
|---|---|---|
| Norfloxacin | 50 g | preparation by precipitation |
| 20% weight/weight NaOH solution | 55.2 g | |

60.
| | | |
|---|---|---|
| Norfloxacin | 50 g | preparation by precipitation |
| 20% weight/weight NaOH solution | 55.2 g | |
| Citric acid | 17.9 g | |
| Tylopur C 300 P ® | 2.0 g | |
| Water | 907.3 g | pH = 6.7 |

61.
| | | |
|---|---|---|
| Norfloxacin | 50 g | preparation by precipitation |
| 20% weight/weight NaOH solution | 55.2 g | |
| Citric acid | 17.9 g | |
| Tylopur C 300 P ® | 5.0 g | |
| Water | 904.3 g | pH = 6.5 |

62.
| | | |
|---|---|---|
| Ofloxacin | 50 g | preparation by precipitation |
| 20% weight/weight NaOH solution | 55.2 g | |
| Citric acid | 17.9 g | |
| Tylopur C 300 P ® | 7.5 g | |
| Water | 901.8 g | pH = 6.5 |

63.
| | | |
|---|---|---|
| Ofloxacin | 50 g | preparation by precipitation |
| 20% weight/weight NaOH solution | 55.2 g | |
| Citric acid | 17.9 g | |
| Tylopur C 300 P ® | 7.5 g | |
| Water | 899.5 g | pH = 6.5 |

64.
| | | |
|---|---|---|
| Ofloxacin | 50 g | preparation by precipitation |
| 20% weight/weight NaOH solution | 55.2 g | |
| Citric acid | 16.0 g | |
| Tylopur C 300 P ® | 2.0 g | |
| Water | 909.2 g | pH = 7.8 |

65.
| | | |
|---|---|---|
| Ofloxacin | 50 g | preparation by precipitation |
| 20% weight/weight NaOH solution | 55.2 g | |
| Citric acid | 24.7 g | |
| Tylopur C 300 P ® | 2.0 g | |
| Water | 900.5 g | pH = 5.3 |

66.
| | | |
|---|---|---|
| Norfloxacin | 50 g | preparation by precipitation |
| 20% weight/weight NaOH solution | 55.2 g | |
| Citric acid | 17.9 g | |
| Tylopur C 300 P ® | 2.0 g | |
| Tween 20 ® | 2.0 g | |
| Water | 900.5 g | pH = 6.9 |

-continued

67.
| | | |
|---|---|---|
| Ofloxacin | 5.0 g | preparation by precipitation |
| 20% weight/weight NaOH solution | 9.43 g | |
| Lipoid E 80 ® | 0.2 g | |
| Citric acid | 1.8 g | |
| Tylopur C 300 P ® | 0.2 g | |
| Water | 77.17 g | |

68.
| | | |
|---|---|---|
| Pefloxacin | 50.0 g | preparation by precipitation |
| Methanesulphonic acid | 16.15 g | |
| 10% weight/weight NaOH solution | 10.83 ml | |
| Water | 400.8 g | pH = 7.0 |

69.
| | | |
|---|---|---|
| Norfloxacin | 50.0 g | preparation by precipitation |
| Methanesulphonic acid | 16.15 g | |
| L-Arginine | 6.11 g | |
| Water | 407.33 g | |

70.
| | | |
|---|---|---|
| Norfloxacin | 50.0 g | preparation by precipitation |
| Methanesulphonic acid | 16.15 g | |
| Trimethanol (tris) | 4.41 g | |
| Water | 408.3 g | pH = 7.0 |

71.
| | | |
|---|---|---|
| Micronized norfloxacin hydrate (85.5%) | 5.85 g | Suspension of micronized norfloxacin hydrate in the aqueous phase |
| Tylopur C 300 P ® | 0.2 g | |
| Anhydrous glycerol | 2.5 g | |
| Water | to 100 ml | |

72.
| | | |
|---|---|---|
| Micronized ofloxacin hydrate (85.5%) | 5.85 g | Suspension of micronized norfloxacin hydrate in the aqueous phase |
| Tylopur C 300 P ® | 0.75 g | |
| Anhydrous glycerol | 2.5 g | |
| Water | to 100 ml | |

73.
| | | |
|---|---|---|
| Micronized amifloxacin hydrate (85.5%) | 5.85 g | Suspension of micronized norfloxacin hydrate in the aqueous phase pH 6.8 |
| Tylopur C 300 P ® | 0.75 g | |
| Tween 80 ® | 0.2 g | |
| Anhydrous glycerol | 2.5 g | |
| Water | to 100 ml | |

74.
| | | |
|---|---|---|
| Micronized pefloxacin hydrate (85.5%) | 5.85 g | Suspension of micronized norfloxacin hydrate in the aqueous phase pH 6.8 |
| Tylopur C 300 P ® | 0.75 g | |
| Lipoid E 80 ® | 0.2 g | |
| Anhydrous glycerol | 2.5 g | |
| Water | to 100 ml | |

75.
| | | |
|---|---|---|
| Micronized enrofloxacin hydrate (85.5%) | 5.85 g | Suspension of micronized enrofloxacin hydrate in the aqueous phase pH 6.8 |
| Tylopur C 300 P ® | 0.2 g | |
| Tween 80 ® | 0.2 g | |
| Anhydrous glycerol | 2.5 g | |
| Water | to 100 ml | |

76.
| | | |
|---|---|---|
| Micronized enrofloxacin hydrate (85.5%) | 5.85 g | Suspension of micronized enrofloxacin hydrate in the aqueous phase pH 6.8 |
| Tylopur C 300 P ® | 0.2 g | |
| Lipoid 80 ® | 0.2 g | |
| Anhydrous glycerol | 2.5 g | |
| Water | to 100 ml | |

77.
| | | |
|---|---|---|
| Enrofloxacin hydrate (85.5%) | 5.85 g | Suspension of micronized enrofloxacin hydrate in the aqueous phase pH 7 |
| Tylopur C 300 P ® | 0.2 g | |
| Lipoid E 80 ® | 0.2 g | |
| Water | 90.0 ml | |

78.
| | | |
|---|---|---|
| Enrofloxacin hydrate (85.5%) | 5.85 g | Suspension of micronized enrofloxacin hydrate in the aqueous phase pH 7 |
| Tylopur C 300 P ® | 0.2 g | |
| Citrate buffer solution pH 7 | 90.0 ml | |
| Lipoid E 80 ® | 0.2 g | |

79.

-continued

| | | |
|---|---|---|
| Enrofloxacin hydrate (85.5%) | 5.85 g | Suspension of micronized enrofloxacin hydrate in the aqueous phase pH 7 |
| Tylopur C 300 P ® | 0.2 g | |
| Phosphate buffer solution pH 7 | 90.0 g | |
| Lipoid E 80 ® | 0.2 ml | |

80.

| | | |
|---|---|---|
| Active compound A | 5.0 g | preparation by precipitation |
| 20% weight/weight NaOH solution | 2.27 g | |
| 85% $H_3PO$ solution | 1.07 g | |
| Tylopur C 300 P ® | 0.2 g | |
| Water | 93.14 g | |

81.

| | | |
|---|---|---|
| Active compound B | 50.0 g | pH 7 |
| 20% weight/weight NaOH solution | 55.5 g | pH 7 osmolality: 285 m osmol/kg |
| Citric acid fine grit | 17.9 g | |
| Water | 903.6 g | |

Particle size <10 μm
Precipitation under aseptic conditions via a reaction jet 60/40 bar and high pressure homogenization under 400 bar.

82.

| | | |
|---|---|---|
| Active compound C | 100.0 g | |
| 20% weight/weight NaOH solution | 62.0 g | |
| Citric acid fine grit | 19.8 g | |
| Water | 869.2 g | |
| Particle size | 2-5 lm | (90% under 10 μm) |

Precipitation under aseptic conditions via a reaction jet 60/40 bar and high pressure homogenization under 400 bar.

83.

| | | |
|---|---|---|
| Active compound A | 100.0 g | |
| 20% weight/weight NaOH solution | 62.0 g | |
| Citric acid fine grit | 19.8 g | |
| Tween 80 ® | 0.1 g | |
| Water | 869.2 g | pH 7.0 |

84.

| | | |
|---|---|---|
| Active compound B | 100.0 g | |
| 20% weight/weight NaOH solution | 62.0 g | |
| Citric acid fine grit | 19.8 g | |
| Tween 80 ® | 1.0 g | |
| Water | 868.2 g | pH 7.0 |

85.

| | | |
|---|---|---|
| Active compound B | 100.0 g | |
| 20% weight/weight NaOH solution | 62.0 g | |
| Citric acid fine grit | 19.8 g | |
| Tween 80 ® | 2.0 g | |
| Water | 867.1 g | pH 7.0 |

86.

| | | |
|---|---|---|
| Active compound A | 100.0 g | |
| 20% weight/weight NaOH solution | 62.0 g | |
| Citric acid fine grit | 19.8 g | |
| Tween 80 ® | 2.0 g | |
| Water | 867.1 g | pH 7.0 |

87.

| | | |
|---|---|---|
| Active compound B | 40.0 g | preparation by precipitation |
| 20% weight/weight NaOH solution | 24.8 g | |
| Citric acid fine grit | 7.92 g | |
| Lipoid E 75 ® | 4.0 g | |
| Water | 343.6 g | pH 7.0 |

88.

| | | |
|---|---|---|
| Active compound B | 200.0 g | preparation by precipitation |
| 20% weight/weight NaOH solution | 62.8 g | |
| Citric acid fine grit | 41.88 g | |
| Water | 738.27 g | pH 7.05 |

89.

| | | |
|---|---|---|
| Active compound C | 20.0 g | preparation by precipitation |
| 20% weight/weight NaOH solution | 12.4 g | |
| 15% weight/weight $H_3PO$ solution | 21.38 ml | |
| Water | to 100 ml | pH 7.05 |

90.

| | | |
|---|---|---|
| Active compound B | 15.0 g | preparation by precipitation |
| 20% weight/weight NaOH solution | 12.4 g | |
| 15% weight/weight $H_3PO$ solution | 16.05 ml | |
| Water | to 100 ml | |

91.

| | | |
|---|---|---|
| Active compound A | 20.0 g | preparation by precipitation |
| 20% weight/weight NaOH solution | 11.25 g | |
| 20% weight/weight lactic acid solution | 3.72 g | |
| 15% weight/weight $H_3PO_4$ solution | 21.5 ml | |
| Water | to 100 ml | pH 7.0 |

92.

| | | |
|---|---|---|
| Active compound B | 20.0 g | preparation by precipitation |
| 20% weight/weight NaOH solution | 10.0 g | |
| 20% weight/weight lactic acid solution | 7.44 g | |
| 15% weight/weight $H_3PO_4$ solution | 12.0 ml | |
| Water | to 100 ml | pH 7.0 |

93.

| | | |
|---|---|---|
| Active compound B | 20.0 g | preparation by precipitation |
| 20% weight/weight NaOH solution | 8.75 g | |
| 20% weight/weight lactic acid solution | 11.16 g | |
| 15% weight/weight $H_3PO_4$ solution | 6.7 ml | |
| Water | to 100 ml | pH 7.0 |

94.

| | | |
|---|---|---|
| Active compound C | 20.0 g | preparation by precipitation |
| 20% weight/weight NaOH solution | 12.4 g | |
| 20% weight/weight lactic acid solution | 21.1 ml | |
| Tylopur C 300 P ® | 0.05 g | |
| Water | to 100 ml | pH 7.0 |

95.

| | | |
|---|---|---|
| Active compound C | 20.0 g | preparation by precipitation |
| 20% weight/weight NaOH solution | 12.4 g | |
| 15% weight/weight $H_3PO_4$ solution | 21.1 ml | |
| HPC | 0.05 g | |
| Water | to 100 ml | pH 7.0 |

96.

| | | |
|---|---|---|
| Active compound B | 20 g | preparation by precipitation |
| 20% weight/weight NaOH solution | 12.4 g | |
| 15% weight/weight $H_3PO_4$ solution | 21.1 ml | |
| Tween 80 ® | 0.05 g | |
| Water | to 100 ml | pH 7.0 |

97.

| | | |
|---|---|---|
| Active compound C | 20.0 g | preparation by precipitation |
| 20% weight/weight NaOH solution | 12.4 g | |
| 15% weight/weight $H_3PO_4$ solution | 21.1 ml | |
| Tween 80 ® | 1.0 g | |
| Water | to 100 ml | pH 7.0 |

98.

| | | |
|---|---|---|
| Norfloxacin | 5 g | suspension of norfloxacin in oily excipient |

99.

| | | |
|---|---|---|
| Ofloxacin | 10 g | |
| Ethyl oleate | 50 g | |

100.

| | | |
|---|---|---|
| Norfloxacin | 30 g | |
| Ethyl oleate | 50 g | |

101.

| | | |
|---|---|---|
| Norfloxacin | 25 g | |

-continued

| | | |
|---|---|---|
| Ethyl oleate | 50 g | |
| 102. | | |
| Ofloxacin | 5 g | |
| Miglyol 812 ® | 50 g | |
| 103. | | |
| Pefloxacin | 10 g | |
| Miglyol 812 ® | 50 g | |
| 104. | | |
| Active compound A | 15 g | |
| Miglyol 812 ® | 50 g | |
| 105. | | |
| Active compound | 5 g | |
| Peanut oil | 50 g | |
| 106. | | |
| Active compound B | 5 g | |
| Ethyl oleate/phospholipon 100 ® = 99.5/0.5 | 50 g | |
| 107. | | |
| Active compound C | 30 g | |
| Ethyl oleate/phospholipon 100 ® = 99.5/0.5 | 50 g | |
| 108. | | |
| Active compound B | 10 g | |
| Miglyol 812 ®/phospholipon 100 ® = 99.5/0.5 | 50 g | |
| 109. | | |
| Active compound A | 15 g | |
| Miglyol 812 ®/phospholipon 100 ® = 99.5/0.5 | 50 g | |
| 110. | | |
| Active compound C | 30 g | |
| Ethyl oleate | 50 g | |
| 111. | | |
| Active compound A | 10 g | |
| Miglyol 812 ® | 50 g | |
| 112. | | |
| Active compound B | 2.5 g | |
| Peanut oil | 50 g | |
| 113. | | |
| Active compound B | 30 g | |
| Ethyl oleate | 50 g | |
| Ascorbyl palmitate | 0.1 g | |
| Lecithin (Phospholipon 100 ®) | 0.5 g | |
| 114. | | |
| Active compound C | 25 g | |
| Miglyol 812 ® | 50 g | |
| Ascorbyl palmitate | 0.1 g | |
| Lecithin (Phospholipon 100 ®) | 0.5 g | |
| 115. | | |
| Active compound B | 30 g | |
| Ethyl oleate | 50 g | |
| Ascorbyl palmitate | 0.1 g | |
| Lecithin (Phospholipon 100 ®) | 0.5 g | |
| Benzyl alcohol | 3 g | |
| 116. | | |
| Active compound C | 25 g | |
| Miglyol 812 ® | 50 g | |
| Benzyl alcohol | 3 g | |
| Lecithin (Phospholipon 100 ®) | 0.5 g | |
| Ascorbyl palmitate | 0.1 g | |
| 117. | | |
| Ciprofloxacin hydrochloride | 5.8 g | |
| Benzyl alcohol | 2.0 g | |
| Soy bean lecithin purified | 0.5 g | |
| Medium chain triglycerides DAB9 | ad 100.0 ml | |
| 118. | | |
| Ciprofloxacin hydrochloride | 11.6 g | |
| Benzyl alcohol | 2.0 g | |
| Egg lecithin purified | 0.5 g | |
| Medium chain triglycerides DAB9 | ad 100.0 ml | |
| 119. | | |
| Ciprofloxacin hydrochloride | 11.6 g | |
| Benzyl alcohol | 2.0 g | |
| Soy bean lecithin purified | 5.0 g | |
| Miglyol 812 ® | ad 100.0 ml | |

-continued

| | | |
|---|---|---|
| 120. | | |
| Ciprofloxacin hydrochloride | 11.6 g | |
| Ethanol absolute | 5.0 g | |
| Egg lecithin purified | 5.0 g | |
| Medium chain triglycerides DAB9 | ad 100.0 ml | |
| 121. | | |
| Ciprofloxacin hydrochloride | 11.6 g | |
| Ethanol absolute | 5.0 g | |
| Soy bean lecithin purified | 5.0 g | |
| Lactic acid concentrated | 0.05-1.0 g | |
| Miglyol 812 ® | ad 100 ml | |
| 122. | | |
| Ciprofloxacin lactate | 12.7 g | |
| Benzyl alcohol | 2.0 g | |
| Soy bean lecithin purified | 5.0 g | |
| Medium chain triglycerides | ad 100.0 ml | |
| 123. | | |
| Ciprofloxacin mesilate | 13.42 g | |
| Ethanol | 10.0 g | |
| Egg lecithin purified | 10.0 g | |
| Ethyl oleate | ad 100.0 ml | |
| 124. | | |
| Ciprofloxacin lactate | 12.7 g | |
| Ethanol | 5.0 g | |
| Soy bean lecithin purified | 5.0 g | |
| Lactic acid concentrate | 0.05-1.0 g | |
| Miglyol 812 ® | ad 100.0 ml | |
| 125. | | |
| Ciprofloxacin hydrochloride | 11.6 g | |
| Ethanol | 10.0 g | |
| Soy bean lecithin purified | 5.0 g | |
| Methane sulphonic acid | 0.05-1.0 g | |
| Miglyol 812 ® | ad 100.0 ml | |
| 126. | | |
| Ciprofloxacin hydrochloride | 11.6 g | |
| Ethanol | 5.0 g | |
| Soy bean lecithin purified | 5.0 g | |
| Citric acid anhydrous micronized | 0.05-2.0 g | |
| Miglyol 812 ® | ad 100.0 ml | |

It will be appreciated that the instant specification and claims are set forth by way of illustration and not limitation, and that various modifications and changes may be made without departing from the spirit and scope of the present invention.

What is claimed is:

1. An intramuscular injection formulation of a gyrase inhibitor comprising about 0.05 to 70% by weight of a gyrase inhibitor of the formula

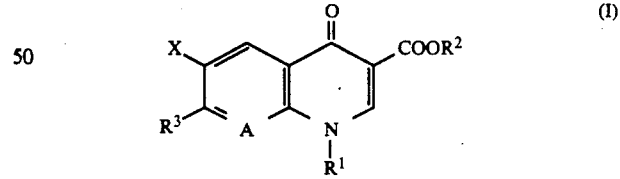

in which

R$^1$ stands for methyl, ethyl, propyl, isopropyl, cyclopropyl, vinyl, 2-hydroxyethyl, 2-fluoroethyl, methoxy, amino, methylamino, dimethylamino, ethylamino, phenyl, 4-fluorophenyl or 2,4-difluorophenyl, R$^2$ stands for hydrogen, alkyl having 1 to 4 carbon atoms or (5-methyl-2-oxo-1,3-dioxol-4-yl)-methyl, R$^3$ stands for methyl or a cyclic amino group of the formula

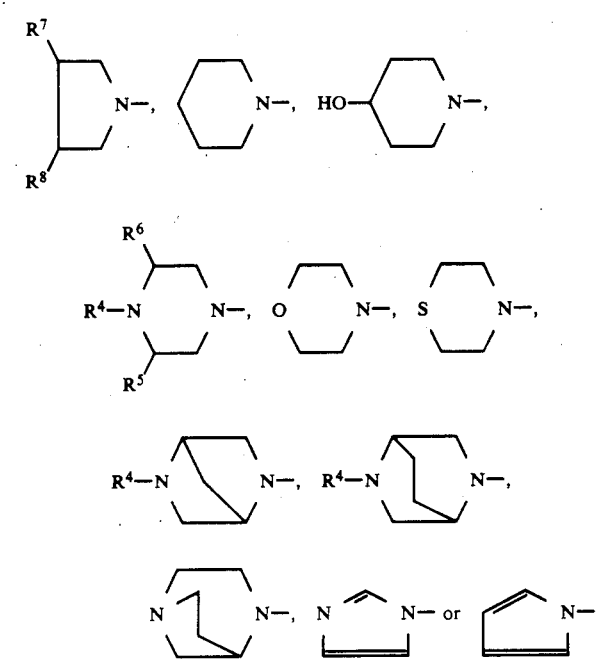

wherein

R[4] stands for hydrogen, alkyl having 1 to 4 carbon atoms, 2-hydroxyethyl, allyl, propargyl, 2-oxopropyl, 3-oxobutyl, phenacyl, formyl, CFCl$_2$-S-, CFCl$_2$-SO$_2$-, CH$_3$O-CO-S-, benzyl, 4-aminobenzyl or

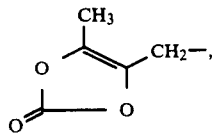

R[5] stands for hydrogen or methyl,

R[6] stands for hydrogen, alkyl having 1 to 4 carbon atoms, phenyl or benzyloxymethyl, R[7] stands for hydrogen, amino, methylamino, ethylamino, aminomethyl, methylaminomethyl, ethylaminomethyl, dimethylaminomethyl, hydroxyl or hydroxymethyl and R[8] stands for hydrogen, methyl, ethyl or chlorine, X stands for fluorine, chlorine or nitro and A stands for N or C-R[6], wherein R[6] stands for hydrogen, halogen, methyl or nitro or, together with R[1], forms a bridge having the structure

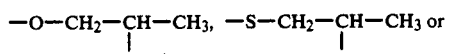

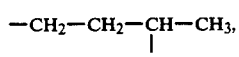

or a salt thereof with an acid or base in oily suspension.

2. An intramuscular injection formulation according to claim 1, wherein the particle size of the gyrase inhibitor is about 0.05–150 μm.

3. An intramuscular injection formulation according to claim 1, wherein the particle size of the gyrase inhibitor is about 4 to 40 μm.

4. An intramuscular injection formulation according to claim 1, containing about 2.5 to 50% by weight of the gyrase inhibitor.

5. A process for the preparation of an intramuscular injection formulation according to claim 1, comprising incorporating an active compound of the formula I, optionally while gassing with nitrogen, into an oil which is initially introduced into the vessel and optionally already contains an antioxidant, stabilizer or surface-active substance, and optionally after-homogenizing the oil.

6. In the treatment of a patient with a gyrase inhibitor, the improvement which comprises administering said gyrase inhibitor intramuscularly in the form of a formulation according to claim 1.

7. An intramuscular injection formulation according to claim 1, comprising an oily suspension and containing the active compound in water-soluble, crystalline or amorphous form as the hydrochloride, lactate, mesylate, p-tolyl sulphonate or salt of another physiologically well-tolerated acid.

8. An intramuscular injection formulation according to claim 1, comprising an oily suspension and containing a well-tolerated tenside selected from the group consisting of soy bean lecithin, egg lecithin, brain lecithin or rape lecithin in a concentration of about 0.1 to 30% W/V.

9. An intramuscular injection formulation according to claim 1, comprising an oily suspension and containing a well-tolerated tenside selected from the group consisting of soy bean lecithin, egg lecithin, brain lecithin or rape lecithin in a concentration of about 0.2 to 10T W/V.

10. An intramuscular injection formulation according to claim 1, comprising an oily suspension and containing a well-tolerated tenside selected from the group consisting of soy bean lecithin, egg lecithin, brain lecithin or rape lecithin in a concentration of about 0.5 to 5% W/V.

11. An intramuscular injection formulation according to claim 7, containing 1 to 300 mmol/1 of physiologically well-tolerated acid in excess of the amount required to form the salt.

12. An intramuscular injection formulation according to claim 7, containing 5 to 50 mmol/1 of physiologically well-tolerated acid in excess of the amount required to form the salt.

13. An intramuscular injection formulation according to claim 7, containing 10 to 30 mmol/1 of physiologically well-tolerated acid in excess of the amount required to form the salt.

14. An intramuscular injection formulation according to claim 11, wherein the acid is lactic acid or citric acid.

15. An intramuscular injection formulation according to claim 1, wherein the gyrase inhibitor is enrofloxacin.

* * * * *

UNITED STATES PATENT AND TRADEMARK OFFICE
CERTIFICATE OF CORRECTION

PATENT NO. : 5,023,257

DATED : June 11, 1991

INVENTOR(S) : Pollinger et al.

It is certified that error appears in the above-identified patent and that said Letters Patent is hereby corrected as shown below:

Title Page    U.S. PATENT DOCUMENTS: After " 4,816,451 " delete " 10/3198 " and substitute -- 3/1989 --

Title Page    FOREIGN PATENT DOCUMENTS: After " 0287926 " delete " 4/1288 " and substitute -- 4/1988 --, after " 0219784 " delete " 4/2987 " and substitute -- 4/1987 --

Signed and Sealed this

Twenty-seventh Day of April, 1993

*Attest:*

MICHAEL K. KIRK

*Attesting Officer*      *Acting Commissioner of Patents and Trademarks*